United States Patent [19]
Young et al.

[11] Patent Number: 5,151,099
[45] Date of Patent: Sep. 29, 1992

[54] TOOL FOR REMOVAL OF PLASTICS MATERIAL

[76] Inventors: Michael J. R. Young, Bremridge Farm, Ashburton, South Devon, England; Brian R. D. Bradnock, 39 Blackford Road, Edinburgh, Scotland

[21] Appl. No.: 804,617

[22] Filed: Dec. 3, 1991

Related U.S. Application Data

[63] Continuation of Ser. No. 499,585, Mar. 27, 1990, abandoned.

[30] Foreign Application Priority Data

Mar. 28, 1989 [GB] United Kingdom ............... 8906898

[51] Int. Cl.⁵ ............... A61B 17/38; A61B 17/00; A61B 17/32; A61F 2/32
[52] U.S. Cl. ............... 606/27; 606/84; 606/92; 606/169
[58] Field of Search ............... 606/84, 85, 86, 92, 606/93, 94, 95, 20, 27, 30, 37, 169

[56] References Cited

U.S. PATENT DOCUMENTS

| | | |
|---|---|---|
| 517,180 | 3/1894 | Wilson ............... 606/27 |
| 718,142 | 1/1903 | Müller ............... 606/27 |
| 2,740,406 | 4/1956 | Tofflemire ............... 606/84 |
| 2,984,241 | 5/1961 | Carlson ............... 606/84 |
| 3,093,135 | 6/1963 | Hirschhorn ............... 808/20 |
| 3,794,040 | 2/1974 | Balamuth ............... 606/27 |
| 4,248,232 | 2/1981 | Engelbrecht ............... 606/169 |
| 4,702,236 | 10/1987 | Tarabichy ............... 606/86 |
| 4,873,969 | 10/1989 | Huebsch ............... 606/92 |
| 5,019,083 | 5/1991 | Klapper ............... 606/86 |

*Primary Examiner*—Robert A. Hafer
*Assistant Examiner*—Michael Brown
*Attorney, Agent, or Firm*—Oblon, Spivak, McClelland, Maier & Neustadt

[57] ABSTRACT

A piezo electric ceramic transducer 1, a coupling horn 2 and a work surface 11 are connected a work horn 3. The work surface is ultrasonically vibrated and heats locally plastics material, causing it to flow through holes 12 in the work surface 11 to a space behind. The material can be removed when the tool is removed from the hole. The tool is particularly useful old cement from bones when revising a joint prosthesis.

9 Claims, 3 Drawing Sheets

TOOL FOR REMOVAL OF PLASTICS MATERIAL

This application is a continuation of application Ser. No. 07/499,585, filed on Mar. 27, 1990, now abandoned.

The present invention relates to a tool for use in removal of plastics material. More particularly, but not exclusively, it relates to a tool for removal of plastics cement from such bores in bones as may be used in hip replacements, or replacements for other joints.

It is now well known to replace damaged or diseased joints in the human or animal body by implants manufactured from combinations of metallic and plastic components. Hereinafter, such replacements will be referred to as "hip joint replacements", although other joints, such as elbows and knees, may be similarly treated.

In a hip joint replacement operation, a metal implant is provided with a long projection which is inserted into a hole drilled in the medulla of the femur and is held firmly in place by means of a plastics cement. On average, such replacements can be expected to last five to ten years. However, due to repetitive shearing forces during daily use, either the bone/cement interface or the cement/metal interface may weaken and the implant will become loose, requiring revision. Sometimes, the metal of the hip replacement may fracture or the plastics components of it may wear out. In these cases, revision is necessary although in most cases the bone/cement interface usually remains quite strong.

In order to revise any loose or damaged implant, all or most of the plastics cement must be removed before inserting a new prosthesis and re-cementing. Removal of the old cement presents a number of difficulties. It is time-consuming and may cause fracturing of the bone. It involves the careful and tedious use of hand tools such as hammers and cement cutting chisels. High speed burrs have been used, but they frequently perforate the bone and make recementing more difficult and not so effective.

It is an object of the present invention to provide a tool for removal of plastics material such as cement from a bore, particularly one in a bone, which overcomes the above disadvantages.

According to the present invention there is provided a tool for use in removing plastics material from a hole comprising a work surface adapted to contact said material, piezo electric transducer means operatively connected through a work horn to said work surface to cause it to vibrate ultrasonically and thereby to heat locally said plastics material, cavity means adapted to receive said heated plastics material and means to connect said cavity means to a working zone adjacent said work surface.

In one embodiment, the work surface comprises a substantially annular cutting edge.

In another embodiment, the work surface comprises a disc adapted to present a substantially planar face to the plastics material to be removed.

Embodiments of the present invention will now be more particularly described by way of example and with reference to the accompanying drawings, in which.

Figure 1:
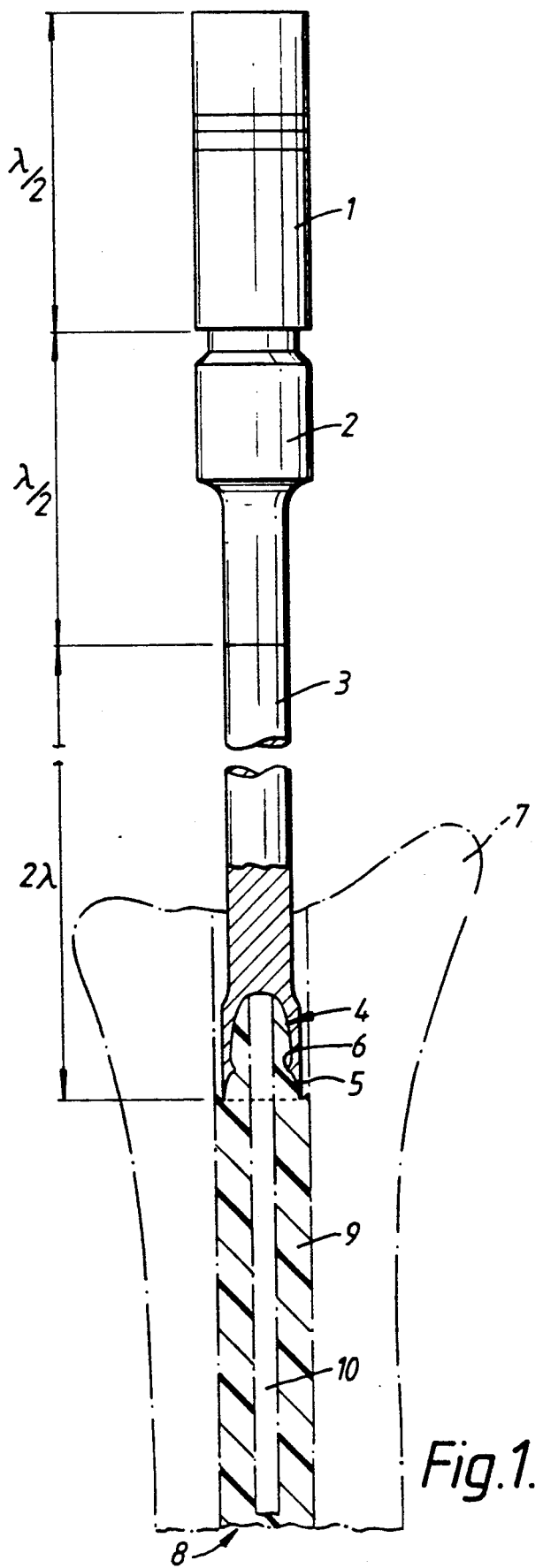
FIG. 1 is a schematic side elevation, shown partially in cross-section, of a tool embodying the invention.
Figure 2:
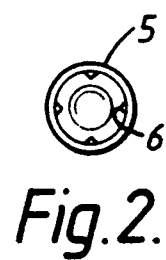
FIG. 2 is an end elevation of the tool of FIG. 1.
Figure 3:
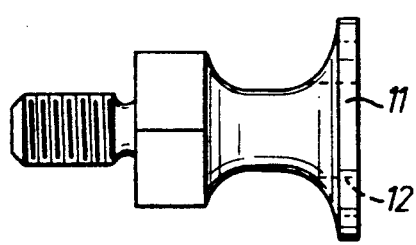
FIG. 3 is a schematic side elevation of an end portion of a tool of a second embodiment of the invention.
Figure 4:
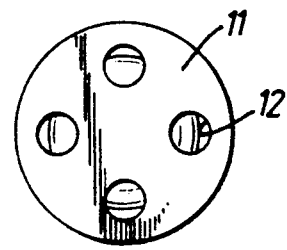
FIG. 4 is an end elevation of the tool end portion of FIG. 3.
Figure 5:
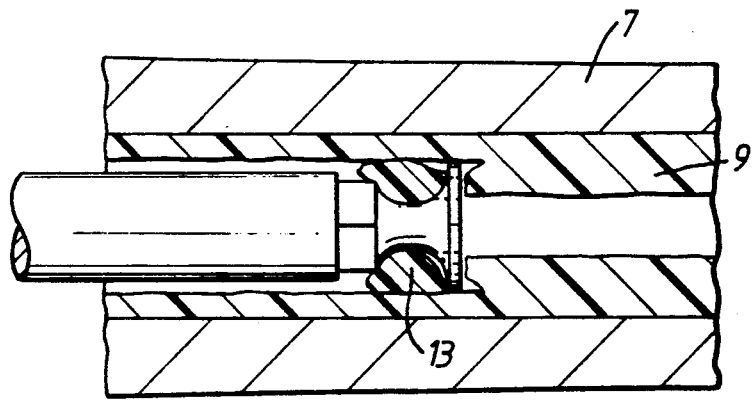
FIG. 5 shows diagrammatically the method of operation of the tool of the second embodiment.

Referring now to the drawings, there is shown in FIGS. 1 and 2, a tool comprising a piezo electric ceramic transducer 1, connected along a longitudinal axis to a coupling horn 2, which in turn is connected along the longitudinal axis to a work horn 3. At the far end of the work horn 3 is a cavity 4 surrounded by an annular cutting edge 5. Within the cavity are provided a number, four are shown, of internal radially extending fins 6, the purpose of which will be described in more detail below.

As shown in the Figures, the length of the piezo electric ceramic transducer 1 is half a wavelength, the length of the coupling horn 2 is also half a wavelength, while the length of the work horn 3 (which includes the annular cutting edge 5) is two wavelengths. However, if it is desired to extract plastics material from a deeper hole, the length of the work horn may be increased providing it remains an integral number of half wavelengths. The term "wavelength" is used to represent the wavelength of the ultrasonic wave generated by the piezo electric ceramic transducer in the material concerned. The preferred material for the work horn and annular cutting edge is titanium or an alloy thereof. At an ultrasonic vibrational frequency in the region of 30–35 kHz, the wavelength of the ultrasonic wave in the titanium alloy is in the region of 70–90 mm.

It is well known that many common plastics materials will transmit high frequency vibrations without the significant internal losses which would cause bulk heating of the material. It is also known that when ultrasound is transmitted through two closely contacted components, the interface can experience a considerable heating effect which under the correct circumstances will produce welding. Such heating can also occur at the interface between a vibrating tool or metal component and the plastics material, the heating being sufficient to melt the plastic. The present invention utilises this effect to drill an annular hole into the plastics material.

The plastics cement material used for hip joint replacements is generally a powder of polymethylmethacrylate beads of diameter less than 100 μm held together in situ by a polymerised methyl methacrylate monomer. This material is prone to creep and is susceptible to localised heating on ultrasonic vibration. The property of creep may be utilised in that, during removal of a core of plastics cement material, the existing cement which remains may be forced into improved engagement with fissures or surface imperfections in the bone by virtue of the ultrasonic vibrations imparted to the cement, and thereby stabilise the interface.

The property of localised heating may also be utilised by the second embodiment of the invention, as shown in FIGS. 3 to 5 and 8. In this case, the work horn 3 terminates in a flat disc 11 in which there are a number of holes 12 (four being shown in FIG. 4). Behind the disc 11 is an annular space connected by means of the holes 12 with the zone of cement being attacked by the ultrasonically vibrated disc 11. The plastics cement melted by the vibration flows through the holes 12 and sets to form an aggregate 13 in the annular space. Every so often, generally after an additional insertion of 5-10 mm, the tool is retracted and this aggregate removed, allowing the tool to be reinserted. In the interval during removal, the cement will cool, thus limiting thermal damage in healthy bone. Cooling may be aided by means of a water or air spray.

Figure 9:
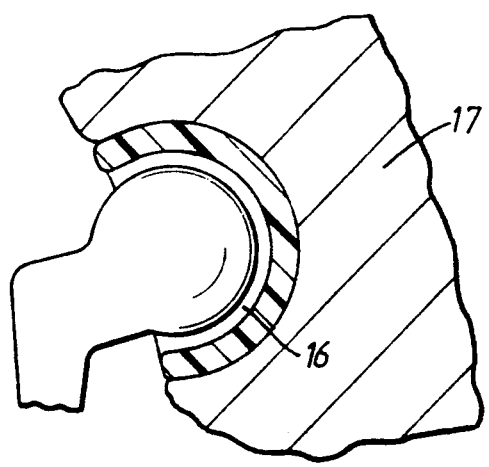
FIG. 9 shows schematically one end of a hip joint.
Figure 10:
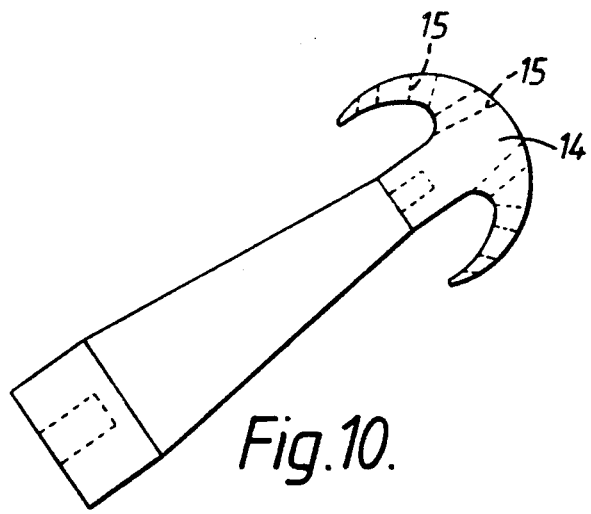
FIG. 10 is a side elevation of a fourth embodiment of tool, adapted for use with a hip socket.

As shown in FIGS. 9 and 10, this principle can be applied also to the ball joint of the hip joint. In this case the disc is replaced by a substantially hemispherical member 14 having a plurality of through holes 15. In operation the member 14 is pushed into cavity 16 of a hip bone 17 and a layer of plastics cement is melted and extruded through holes 15 to the space behind the member 14.

Figure 6:
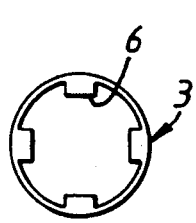
FIG. 6 is an end elevation of a third embodiment of the invention.
Figure 7:
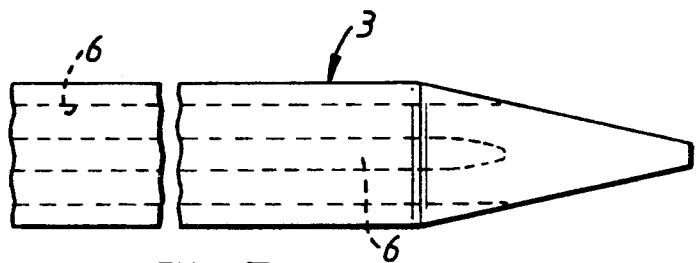
FIG. 7 is a schematic side elevation of the embodiment of FIG. 6.

FIGS. 6 and 7 show a variant of the first embodiment in which the fins 6 are less sharp. In other respects it is similar to the first embodiment.

The present invention is described with reference to removing a plastics cement from a hip joint replacement during revision of the prosthesis. In this case, the hip bone or femur 7 has a blind hole 8 filled with plastics cement 9 which had originally surrounded the prosthesis, but which has a void 10 where the prosthesis used to be.

In order to operate the tool, the tip is inserted a short distance into the plastics material cement 9 and pushed thereinto for about 5-10 mm, as the plastic material softens under the effect of the ultrasonic vibrations. At this point, a core of softened but relatively stiff cement fills the work horn cavity 4, or is lodged in the space behind the disc 11. In the first and third embodiments, the transducer 1 is switched off and the tool rotated manually in order to shear the plastics plug contained within the cavity from the bulk of the bone cavity cement. The presence of the internal fins 6 ensures that an adequate shear stress is generated by preventing rotation of the entrained core with respect to the tool.

The tool is then withdrawn, together with the small plug of cement within the cavity, and the plug is removed by blowing compressed air down an axial duct (not shown) in the work horn 3. If so desired, a vacuum may be applied to the cavity through the axial duct during the step of withdrawal of the tool in order to ensure that the plug remains within the cavity 4.

In the case of the second and fourth embodiments, the tool is simply withdrawn, bringing with it the aggregated mass of plastics cement.

The sequence is then repeated until the cement is removed from the bore to an appropriate depth. It would be possible to incorporate a small intrascope coaxially within an axial duct in order to facilitate visual inspection of the cutting operation.

Use of the tool embodying the present invention results in a much faster cutting operation and also allows the possibility of leaving intact a thin layer of cement which is characteristically well-bonded to the living bone tissue when revising damaged but not loose implants. If the cement is already well-bonded, the strength of the revised implants would be significantly improved. The apparatus also may permit improved bonding between bone and existing cement. Whereas the existing methods of revision of hip joint prostheses may have required several hours to remove the existing cement, for all of which the patient must be anaesthetised, the present invention allows removal of existing cement, at least sufficient for revision, within a period of less than one hour. The work horn 3 may be curved to suit penetration of a curved hole in a medulla or similar bone.

Figure 8:
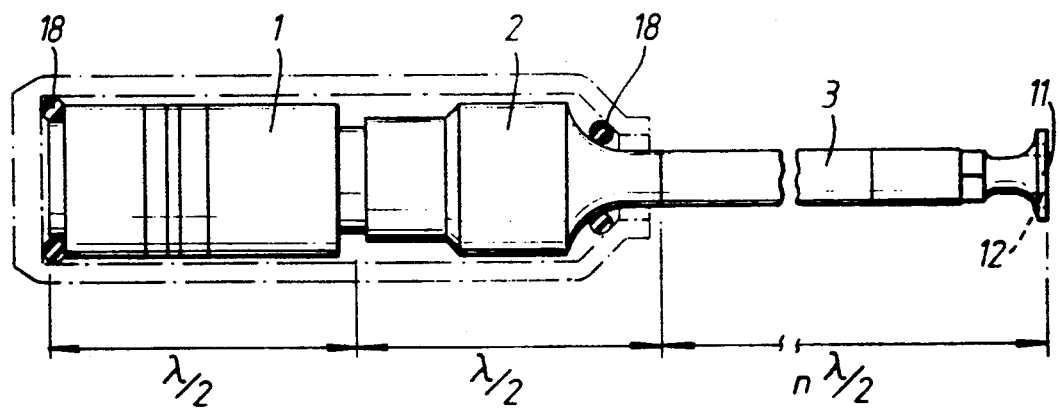
FIG. 8 is a longitudinal sectional view of a tool according to the second embodiment.

As shown in FIG. 8, the principle of which is applicable to any embodiment, a handle surrounds the transducer 1 and coupling horn 2, but is separated therefrom by 0 rings 18 of neoprene or the like, to ensure that the surgeon is completely insulated from ultrasonic emissions.

What we claim is:

1. A tool for use in removing heat softenable plastics material from a hole in which said plastics material is in a substantially solid state comprising a disc having a work surface on one side adapted to contact said material, piezo electric transducer means operatively connected through a work horn to said disc to cause said work surface to vibrate ultrasonically and thereby to heat locally said plastics material until it is softened, cavity means on a second side of said disc opposite said work surface and adapted to receive said heated and softened plastics material, and passage means connecting said cavity means to a working zone of said plastics material ahead of said disc when engaged by said work surface to enable heated and softened plastics material to flow through said passage means into said cavity means.

2. A tool as claimed in claim 1, wherein said work surface is substantially planar.

3. A tool as claimed in claim 1 including a support for said disc on said second side thereof and wherein said cavity means comprises an annular space between said support and an internal surface of plastics material remaining after removal of a desired amount of said material.

4. A tool as claimed in claim 3, wherein said passage means comprises at least one hole through said disc to connect said annular space with said working zone.

5. A tool as claimed in claim 1, wherein said work surface comprises a substantially hemispherical surface having apertures therein.

6. A tool as claimed in claim 1, wherein the work horn is of a length equal to an integral number of half wavelengths of the ultrasonic wave in the material of the work horn.

7. A tool as claimed in claim 6, wherein the material of the work horn is a titanium alloy.

8. A tool as claimed in claim 6, wherein the work horn is curved.

9. A method of removing plastics material from a hole comprising the steps of inserting into an end of said hole a disc having a work surface adapted to contact said material and having cavity means rearwardly of said work surface connected by passage means to the front of said work surface, ultrasonically vibrating said disc, forcing said tool inwardly to melt by ultrasonic vibrations some of said plastics material and transfer it through said aperture means to said cavity means, removing said disc from the hole, removing the melted plastics material from the cavity means and repeating the previous steps until a desired amount of plastics material has been removed.

* * * * *

UNITED STATES PATENT AND TRADEMARK OFFICE
CERTIFICATE OF CORRECTION

PATENT NO. : 5,151,099

DATED : September 29, 1992

INVENTOR(S) : Michael J.R. Young et al.

It is certified that error appears in the above-identified patent and that said Letters Patent is hereby corrected as shown below:

Item [57] Abstract,

Line 2, after "connected" insert --by--;

Line 7, after "useful" insert --in removing--.

Signed and Sealed this

Fourteenth Day of September, 1993

Attest:

BRUCE LEHMAN

Attesting Officer

Commissioner of Patents and Trademarks